United States Patent [19]

Fanshawe et al.

[11] 4,088,652

[45] May 9, 1978

[54] ACYLAZABICYCLOHEXANES

[75] Inventors: William Joseph Fanshawe, Pearl River; Joseph William Epstein, Monroe; Lantz Stephen Crawley, Spring Valley, all of N.Y.; Corris Mabelle Hofmann, Ho-Ho-Kus; Sidney Robert Safir, River Edge, both of N.J.

[73] Assignee: American Cyanamid Company, Stamford, Conn.

[21] Appl. No.: 749,578

[22] Filed: Dec. 10, 1976

Related U.S. Application Data

[63] Continuation of Ser. No. 600,559, Jul. 31, 1975, abandoned.

[51] Int. Cl.$^2$ .................................. C07D 221/22
[52] U.S. Cl. ....................................... 260/293.54
[58] Field of Search ................ 260/293.54, 250 Q Primary Examiner—Henry R. Jiles
Assistant Examiner—Richard A. Schwartz
Attorney, Agent, or Firm—Norton S. Johnson

[57] ABSTRACT

Phenyl and substituted phenyl 3-azabicyclo[3.1.0]-hexanes and method of preparing the same are described. They are useful as intermediates in preparing other physiologically active compounds.

9 Claims, No Drawings

ACYLAZABICYCLOHEXANES

This is a continuation of application Ser. No. 600,559 filed July 31, 1975, now abandoned.

This invention is concerned with compounds of the formula:

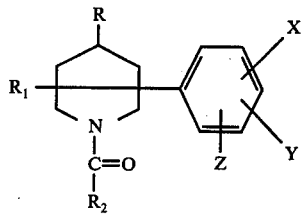

wherein X and Z are hydrogen, halogen or $C_1$-$C_6$ alkoxy; Y is selected from the group consisting of hydrogen, halogen, $C_1$-$C_6$ alkyl, $C_1$-$C_6$ alkoxy, trifluoromethyl, nitro, amino, acetamido and hydroxy; R and $R_1$ are selected from the group consisting of hydrogen and $C_1$-$C_6$ alkyl, and $R_2$ is selected from the group consisting of hydrogen, $C_1$-$C_6$ alkyl, $C_3$-$C_6$ cycloalkyl, $C_2$-$C_6$ alkenyl, $C_2$-$C_6$ alkynyl, phenyl, acetamidophenyl, halophenyl, halophenylmethyl, nitrophenyl, carboxyphenyl, furyl, furfuryl, thienyl, thenyl, adamantyl, quinoxalinyl, naphthyl and norbornyl.

The compounds of this invention are useful as intermediates for the preparation of the anxialytic or analgesic agents of Application Ser. No. 601,128 filed July 31, 1975, now abandoned.

The compounds of the present invention may be prepared as follows:

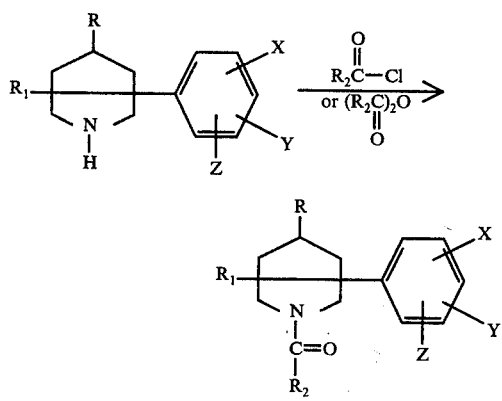

A compound of formula (I) is reacted with an acyl chloride or an acyl anhydride, wherein R, $R_1$, $R_2$, X, Y and Z are as described above, in a solvent such as benzene at 25°–70° C. for 1–18 hours with an acid binding agent such as sodium carbonate or triethylamine to produce the compounds of formula (II).

Alternatively the compounds of the present invention may be prepared as follows:

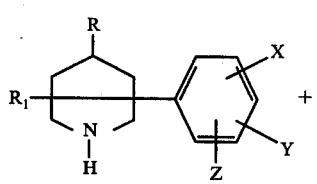

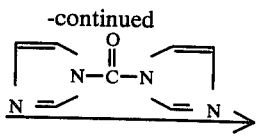

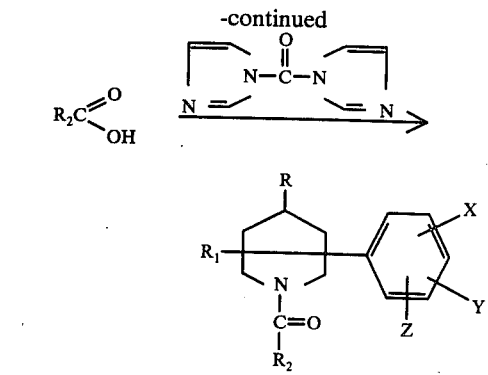

A compound of formula (I) is reacted with a carboxylic acid (III), wherein R, $R_1$, $R_2$, X, Y and Z are as described above and N,N'-carbonyldiimidazole, in an aprotic solvent such as tetrahydrofuran, benzene or ether, at 25°–50° C. for 30–120 minutes. The reaction mixture is evaporated, water is added and the product (II) is extracted with a solvent such as benzene, chloroform or methylene chloride.

The starting material for the preparation of compounds of the present invention are generally described in the prior art such as U.S. Pat. Nos. 3,166,571 and 3,344,026. Others can be prepared by a simple modification of the procedures described in the above patents.

The compounds of this invention such as that of Example 1 hereinafter, can be reacted with, for example, sodium bis(2-methoxyethoxy)aluminum hydride to produce 3-cyclopropylmethyl-1-phenyl-3-azabicyclo[3.1.0]hexane hydrochloride. The latter compound is useful for its anxiolytic and analgesic activity. Likewise other products of this invention such as 3-p-chlorobenzoyl-1-(p-chlorophenyl)-3-azabicyclo[3.1.0]hexane can be reacted with, for example, sodium bis(2-methoxyethoxy)aluminum hydride to produce 3-(p-chlorobenzyl)-1-(p-chlorophenyl)-3-azabicyclo[3.1.0]hexane having anxiolytic and analgesic activity. Other compounds of this invention can be reacted in a similar manner to give physiologically active products.

The following examples describe the preparation of specific compounds of this invention.

EXAMPLE 1

Preparation of 3-Cyclopropylcarbonyl-1-phenyl-3-azabicyclo[3.1.0]-hexane

To a stirred slurry of 61.2 g. of 1-phenyl-1,2-cyclopropanedicarboximide (U.S. Pat. No. 3,166,571 — Example VIII) in 2 liters of benzene is added 400 ml. of sodium bis(2-methoxyethoxy)aluminum hydride 70% solution in benzene under nitrogen. The mixture is stirred at room temperature for 2 hours, refluxed for 4 hours and then stirred at room temperature for 20 hours. A 400 ml. portion of 10N sodium hydroxide is added cautiously with stirring. The organic layer is washed twice with dilute sodium hydroxide and then with water, dried over magnesium sulfate and evaporated to give an amber oil. This oil is dissolved in dilute hydrochloric acid, washed with ether, filtered and the filtrate made basic with sodium hydroxide. The basic filtrate is extracted with benzene, dried over magnesium sulfate, filtered and evaporated to give 1-phenyl-3-azabicyclo[3.1.0]hexane as an amber oil.

To a solution of 15.9 g. of 1-phenyl-3-azabicyclo-[3.1.0]hexane in 100 ml. of benzene and 20 ml. of triethylamine is added 11.0 g. of cyclopropanecarboxylic acid chloride in 20 ml. of benzene over 5 minutes. The mixture is stirred for 30 minutes and 50 ml. of water is added. The benzene layer is extracted with dilute sodium bicarbonate followed by dilute hydrochloric acid and then water, dried over magnesium sulfate and evaporated to give the product as a brown oil.

EXAMPLE 2

Preparation of
3-Acetyl-1-phenyl-3-azabicyclo[3.1.0]hexane

To 15.9 g. of 1-phenyl-3-azabicyclo[3.1.0]hexane in 20 ml. of pyridine is added 20 ml. of acetic anhydride. The mixture is allowed to stand overnight at room temperature and then evaporated to give an oil. This oil is dissolved in a mixture of ether and methylene chloride, washed with dilute hydrochloric acid and then sodium bicarbonate and dried over magnesium sulfate and evaporated to a pale amber liquid. This liquid is crystallized from hexane to give the product, mp 63°–65° C.

EXAMPLE 3

Preparation of
o-(1-Phenyl-3-azabicyclo[3.1.0]hex-3-ylcarbonyl)benzoic acid

A mixture of 7.95 g. of 1-phenyl-3-azabicyclo-[3.1.0]hexane and 7.4 g. of phthalic anhydride in 300 ml. of toluene is refluxed for ½ hour and then allowed to stand overnight. The solution is extracted three times with 1N sodium hydroxide and made extremely acid with 1N hydrochloric acid. The solid which separates is extracted with chloroform, dried over magnesium sulfate, filtered and filtrate evaporated to a glass residue. This glass is triturated in hexane and filtered giving the product as a light pink solid, IR 5.85, 6.10μ.

EXAMPLE 4

Preparation of
2'-(1-Phenyl-3-azabicyclo[3.1.0]-hex-3-ylcarbonyl)acetanilide

A mixture of 7 g. of 1-phenyl-3-azabicyclo[3.1.0]hexane and 6.5 g. of isatoic anhydride in 10 ml. of dimethyl sulfoxide is warmed on a steam bath for 10 minutes. The mixture is cooled and water is added producing a gummy solid which is separated by extraction with chloroform, dried, filtered and evaporated to a dark oil. This oil is dissolved in 30 ml. of acetic anhydride, refluxed for 5 minutes, evaporated to an oil and water is added and decanted from the mixture several times. The thick oil is mixed with ethanol and a solid separates. This solid is dissolved in hot ethanol filtered and cooled giving a white solid which is recrystallized once from aqueous ethanol and once from ether to give the product as a white solid, mp 124.5°–127° C.

EXAMPLE 5

Preparation of
3-Cyclohexylcarbonyl-1-phenyl-3-azabicyclo[3.1.0]-hexane

A 6.4 g. portion of 1-phenyl-3-azabicyclo[3.1.0]hexane is added to 60 ml. of benzene. A 4.2 g. portion of sodium carbonate in 40 ml. of water is added with stirring. A 5.9 g. portion of cyclohexylcarbonyl chloride in 40 ml. of benzene is added and the mixture is stirred overnight. The oily solid in the aqueous layer is extracted with chloroform. The extracts are washed with water and dilute hydrochloric acid, dried over magnesium sulfate, filtered and evaporated. The oily residue is extracted with ether giving a white solid as the product, mp 81°–82° C.

EXAMPLE 6

Preparation of
3-p-Fluorobenzoyl-1-phenyl-3-azabicyclo[3.1.0]hexane

A 6.4 g. portion of 1-phenyl-3-azabicyclo[3.1.0]-hexane is added to 60 ml. of benzene. A 4.2 g. portion of sodium carbonate in 40 ml. of water is added with stirring. A 6.3 g. portion of p-fluorobenzoyl chloride in 40 ml. of benzene is added and the mixture is stirred overnight. The solid in the aqueous layer is recovered by filtration, washed with water and slurried in ether giving the product as white crystals, mp 101°–103° C.

EXAMPLE 7

Preparation of
3-m-Fluorobenzoyl-1-phenyl-3-azabicyclo[3.1.0]hexane

A 6.4 g. portion of 1-phenyl-3-azabicyclo[3.1.0]-hexane is added to 60 ml. of benzene. A 4.2 g. portion of sodium carbonate in 40 ml. of water is added with stirring. A 6.3 g. portion of m-fluorobenzoyl chloride is added and the mixture is stirred overnight. The oil present in the aqueous layer is extracted with chloroform, washed successively with water, dilute hydrochloric acid and water, dried over magnesium sulfate, filtered and evaporated giving an oil. This oil is dissolved in ether. A small amount of petroleum ether is added and the product is recovered as a white solid, mp 68°–69.5° C.

EXAMPLE 8

Preparation of
3-p-Nitrobenzoyl-1-(p-chlorophenyl)-3-azabicyclo[3.1.0]hexane

Following the procedure described in Example 1 the compound 1-(p-chlorophenyl)-1,2-cyclopropanedicarboximide (U.S. Pat. No. 3,344,026—Example 1) is reduced with sodium bis(2-methoxyethoxy)aluminum hydride 70% solution in benzene to produce the compound 1-p-chlorophenyl-3-azabicyclo[3.1.0]hexane.

A 19.35 g. portion of 1-p-chlorophenyl-3-azabicyclo[3.1.0]hexane is dissolved in 150 ml. of benzene. A 10.59 g. portion of sodium carbonate in 100 ml. of water is added with stirring. An 18.45 g. portion of p-nitrobenzoyl chloride in 100 ml. of benzene is added slowly to the rapidly stirred mixture. The mixtue is stirred for 1 hour and then allowed to stand overnight at room temperature. The product is recovered by filtration, washed successively with dilute sodium carbonate, 0.5N hydrochloric acid and then water and dried yielding the product as a white solid, mp 177°–180° C.

EXAMPLE 9

Preparation of
3-p-Chlorobenzoyl-1-(p-chlorophenyl)-3-azabicyclo[3.1.0]hexane

Following the procedure of Example 8, 19.35 g. of 1-p-chlorophenyl-3-azabicyclo[3.1.0]hexane, 10.59 g. of sodium carbonate and 17.5 g. of p-chlorobenzoyl chloride are reacted. The benzene is evaporated and the dark purple residue is dissolved in 200 ml. of chloroform and washed successively with 5% sodium carbonate, 0.5N Hydrochloric acid and then with water and dried over sodium sulfate giving a dark purple oil. The oil is extracted with ether giving the product as grey crystals, mp 98°–100° C.

EXAMPLE 10

Preparation of 3-(2-Furoyl)-1-(p-chlorophenyl)-3-azabicyclo[3.1.0]-hexane

Following the procedure of Example 8, 19.35 g. of 1-p-chlorophenyl-3-azabicyclo[3.1.0]hexane, 10.59 g. of sodium carbonate and 13.05 g. of 2-furoyl chloride are reacted to produce the product as a dark brown gum.

EXAMPLE 11

Preparation of 3-m-Fluorobenzoyl-1-(p-chlorophenyl)-3-azabicyclo[3.1.0]hexane

Following the procedure of Example 8, 19.35 g. of 1-p-chlorophenyl-3-azabicyclo[3.1.0]hexane, 10.59 g. of sodium carbonate and 15.8 g. of m-fluorobenzoyl chloride are reacted to give the product as a brown oil. The oil is dissolved in 100 ml. of ether and 30 ml. of petroleum ether is added. The product is recovered as a white solid by filtration, washed with ether and air dried, mp 70°–73° C.

EXAMPLE 12

Preparation of 3-o-Fluorobenzoyl-1-(-p-chlorophenyl)-3-azabicyclo[3.1.0]hexane

Following the procedure of Example 8, 19.53 g. of 1-p-chlorophenyl-3-azabicyclo[3.1.0]hexane, 10.59 g. of sodium carbonate and 15.8 g. of o-fluorobenzoyl chloride are reacted to give the product as a brown gum.

EXAMPLE 13

Preparation of 3-(2-Naphthylcarbonyl)-1-chlorophenyl)-3-azabicyclo[3.1.0]hexane

Following the procedure of Example 8, 19.53 g. of 1-p-chlorophenyl-3-azabicyclo[3.1.0]hexane, 10.59 g. of sodium carbonate and 19.0 g. of 2-naphthylcarbonyl chloride are reacted to produce the product, which after washing with ether and drying, is recovered as a white solid, mp 126°–129° C.

EXAMPLE 14

Preparation of 3-p-Fluorobenzoyl-1-(p-chlorophenyl)-3-azabicyclo[3.1.0]hexane

Following the procedure of Example 8, 19.35 g. of 1-p-chlorophenyl-3-azabicyclo[3.1.0]hexane, 10.59 g. of sodium carbonate and 15.8 g. of p-fluorobenzoyl chloride are reacted. Ether extraction of the reaction product gives a white solid, mp 130°–132° C.

EXAMPLE 15

Preparation of 3-(5-Norbornen-2-ylcarbonyl)-1-(p-chlorophenyl)-3-azabicyclo[3.1.0]hexane Following the procedure of Example 8, 19.53 g. of 1-p-chlorophenyl-3-azabicyclo[3.1.0]hexane, 10.59 g. of sodium carbonate and 5-norbornene-2-carbonyl chloride are reacted to give the product as a light brown-yellow oily gum.

EXAMPLE 16

Preparation of 3-(1-Adamantylcarbonyl)-1-(p-chlorophenyl)-3-azabicyclo[3.1.0]hexane Following the procedure of Example 8, 19.35 g. of 1-p-chlorophenyl-3-azabicyclo[3.1.0]hexane, 10.59 g. of sodium carbonate and 19.87 g. of 1-adamantanecarboxylic acid chloride are reacted, yielding the product as a white solid, mp 163°–165° C.

EXAMPLE 17

Preparation of 3-Acetyl-1-(p-nitrophenyl)-3-azabicyclo[3.1.0]hexane

To a suspension of 3-acetyl-1-phenyl-3-azabicyclo[3.1.0]hexane in concentrated sulfuric acid is added concentrated nitric acid during 15 minutes at 0°–10° C. The resulting mixture is stirred at room temperature for 15 minutes and then poured onto ice. The product, 3-acetyl-1-(p-nitrophenyl)-3-azabicyclo[3.1.0]hexane, is collected by filtration.

EXAMPLE 18

Preparation of 3-Acetyl-1-(p-aminophenyl)-3-azabicyclo[3.1.0]hexane

A solution of 3-acetyl-1-(p-nitrophenyl)-3-azabicyclo[3.1.0]hexane in tetrahydrofuran is hydrogenated at atmospheric pressure and ambient temperature using a 5% palladium on charcoal catalyst. Filtration and evaporation of the filtrate under reduced pressure gives 3-acetyl-1-(p-aminophenyl)-3-azabicyclo[3.1.0]hexane.

EXAMPLE 19

Preparation of 3-Acetyl-1-(p-hydroxyphenyl)-3-azabicyclo[3.1.0]hexane

A solution of 3-acetyl-1-(p-aminophenyl)-3-azabicyclo[3.1.0]hexane in 8N hydrochloric acid is diazotized at 0° C, with aqueous sodium nitrite. The solution is then allowed to stand at ambient temperature until the evolution of nitrogen ceases. This mixture is then extracted with ether, and the extract is dried over sodium sulfate, filtered and then evaporated under reduced pressure to give 3-acetyl-1-(p-hydroxyphenyl)-3-azabicyclo[3.1.0]hexane.

EXAMPLE 20

Preparation of 3-Acetyl-1-(p-acetamidophenyl)-3-azabicyclo[3.1.0]-hexane

A solution of 3-acetyl-1-(p-aminophenyl)-3-azabicyclo[3.1.0]hexane in aqueous acetic acid-sodium acetate is treated with acetic anhydride at ambient temperature. The reaction mixture is chilled and filtered to give 3-acetyl-1-(p-acetamidophenyl)-3-azabicyclo[3.1.0]hexane.

EXAMPLE 21

Preparation of 3-Acetyl-1-(p-methoxyphenyl)-3-azabicyclo[3.1.0]hexane

To a stirred mixture of 1-(p-methoxyphenyl)-3-azabicyclo[3.1.0]hexane in benzene and aqueous sodium carbonate is added acetyl chloride and the mixture is stirred at ambient temperature for 18 hours. Benzene is removed by evaporation under reduced pressure, and filtration of the residual mixture gives 3-acetyl-1-(p-methoxyphenyl)-3-azabicyclo[3.1.0]hexane.

In a like manner the following compounds are synthesized as outlined below:

1. 1-(α,α,α-trifluoro-p-tolyl)-3-azabicyclo[3.1.0]hexane, and benzoyl chloride give 3-benzoyl-1-(α,α,α,-trifluoro-p-tolyl)-3-azabicyclo[3.1.0]hexane;
2. 1-(p-tolyl)-3-azabicyclo[3.1.0]hexane and acetyl chloride give 3-acetyl-1-(p-tolyl)-3-azabicyclo[3.1.0]hexane;
3. 6-methyl-1-phenyl-3-azabicyclo[3.1.0]hexane and acetyl chloride give 3-acetyl-6-methyl-1-phenyl-3-azabicyclo[3.1.0]hexane;
4. 5-methyl-1-phenyl-3-azabicyclo[3.1.0]hexane and acetyl chloride give 3-acetyl-5-methyl-1-phenyl-3-azabicyclo[3.1.0]hexane;
5. 1-phenyl-3-azabicyclo[3.1.0]hexane and acryloyl chloride give 3-acryloyl-1-phenyl-3-azabicyclo[3.1.0]hexane;
6. 1-(p-chlorophenyl)-3-azabicyclo[3.1.0]hexane and propiolyl chloride give 3-propiolyl-1-(p-chlorophenyl)-3-azabicyclo[3.1.0]hexane;
7. 1-phenyl-3-azabicyclo[3.1.0]hexane and (2-furyl)acetyl chloride give 3-(2-furylacetyl)-1-phenyl-3-azabicyclo[3.1.0]hexane;
8. 1-(p-chlorophenyl)-3-azabicyclo[3.1.0]hexane and (2-thienyl)acetyl chloride give 3-(2-thienyl)acetyl-1-(p-chlorophenyl)-3-azabicyclo[3.1.0]hexane;
9. 1-phenyl-3-azabicyclo[3.1.0]hexane and thenoyl chloride give 3-thenoyl-1-phenyl-3-azabicyclo[3.1.0]hexane;
10. 1-(3,4-dichlorophenyl)-3-azabicyclo[3.1.0]hexane and acetyl chloride give 3-acetyl-1-(3,4-dichlorophenyl)-3-azabicyclo[3.1.0]hexane;
11. 1-(3,4,5-trimethoxyphenyl)-3-azabicyclo[3.1.0]hexane and acetyl chloride give 3-acetyl-1-(3,4,5-trimethoxyphenyl)-3-azabicyclo[3.1.0]hexane;
12. 1-(m-fluorophenyl)-3-azabicyclo[3.1.0]hexane and acetyl chloride give 3-acetyl-1-(m-fluorophenyl)-3-azabicyclo[3.1.0]hexane.

EXAMPLE 22

Preparation of 3-Formyl-1-(p-chlorophenyl)-3-azabicyclo[3.1.0]hexane

A solution of 1-(p-chlorophenyl)-3-azabicyclo[3.1.0]hexane in formic acid is added at 0°–5° C. to aceticformic anhydride prepared from 2 volumes of acetic anhydride and one volume of formic acid. The mixture is warmed to 40°–50° C. and poured onto ice to give 3-formyl-1-(p-chlorophenyl)-3-azabicyclo[3.1.0]hexane as the product.

EXAMPLE 23

Preparation of 3-(p-Fluorophenylacetyl)-1-phenyl-3-azabicyclo[3.1.0]hexane

To a solution of 6.2 g. of p-fluorophenylacetic acid in 60 ml. of dry tetrahydrofuran is added 6.8 g. of N,N'-carbonyl diimidazole. The resultant mixture is allowed to stand 1 hour, at which time the evolution of carbon dioxide has ceased. To this solution is added 6.4 g. of 1-phenyl-3-azabicyclo[3.1.0]hexane and the reaction solution is allowed to stand ½ hour and then warmed on a steam bath for ½ hour. After removal of the solvent, the residue is poured into ice-water and the mixture is extracted with chloroform. The extracts are dried and evaporated to give the product as an amber oil; IR 6.04μ.

EXAMPLE 24

Preparation of 1-(p-Chlorophenyl)-3-(quinoxalin-2-ylcarbonyl)-3-azabicyclo[3.1.0]hexane Using the procedure of Example 5, 1-(p-chlorophenyl)-3-azabicyclo[3.1.0]hexane is treated with quinoxalin-2-ylcarbonyl chloride in benzene and aqueous sodium carbonate to yield the product as off-white crystals, mp 90°–105° C.

We claim:
1. A compound of the formula:

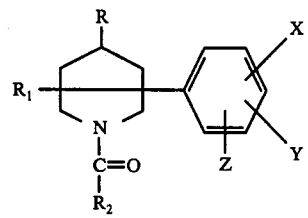

wherein X and Z are selected from the group consisting of hydrogen, halogen and $C_1$-$C_6$ alkoxy; Y is selected from the group consisting of hydrogen, halogen, $C_1$-$C_6$ alkyl, $C_1$-$C_6$ alkoxy, trifluoromethyl, nitro, amino, acetamido and hydroxy; R and $R_1$ are selected from the group consisting of hydrogen and $C_1$-$C_6$ alkyl and $R_2$ is selected from the group consisting of hydrogen, $C_1$-$C_6$ alkyl, $C_3$-$C_6$ cycloalkyl, phenyl, halophenyl, furyl, adamantyl, naphthyl and norbornyl.

2. The compound in accordance with claim 1, 3-cyclopropylcarbonyl-1-phenyl-3-azabicyclo[3.1.0]hexane.

3. The compound in accordance with claim 1, 3-acetyl--phenyl-3-azabicyclo[3.1.0]hexane.

4. The compound in accordance with claim 1, o-(1-phenyl-3-azabicyclo[3.1.0]hex-3-ylcarbonyl) benzoic acid.

5. The compound in accordance with claim 1, 3-cycyohexylcarbonyl-1-phenyl-3-azabicyclo[3.1.0]hexane.

6. The compound in accordance with claim 1, 3-m-fluorobenzoyl-1-phenyl-3-azabicyclo[3.1.0]hexane.

7. The compound in accordance with claim 1, 3-(1-adamantylcarbonyl)-1-(p-chlorophenyl)-3-azabicyclo[3.1.0]hexane.

8. The compound in accordance with claim 1, 3-acetyl-1-(p-aminophenyl)-3-azabicyclo[3.1.0]hexane.

9. The compound in accordance with claim 1, 3-acetyl-1-(p-acetamidophenyl)-3-azabicyclo[3.1.0]hexane.

* * * * *

UNITED STATES PATENT OFFICE
CERTIFICATE OF CORRECTION

Patent No. 4,088,652        Dated    May 9, 1978

Inventor(s)  William Joseph Fanshawe, et al.

It is certified that error appears in the above-identified patent and that said Letters Patent are hereby corrected as shown below:

Column 1, lines 10-15, the formula should appear as follows:

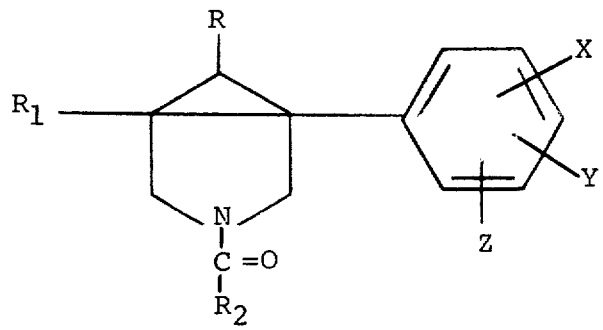

Column 1, lines 36-41, the formula I should appear as follows:

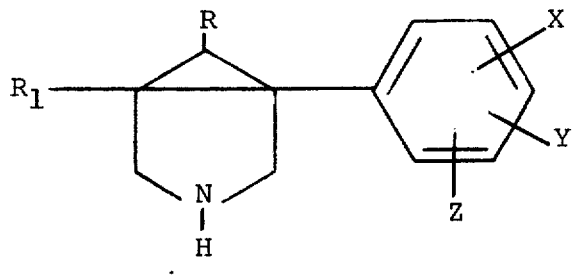

UNITED STATES PATENT OFFICE
CERTIFICATE OF CORRECTION

Patent No. 4,088,652　　　　　Dated May 9, 1978

Inventor(s) William Joseph Fanshawe, et al.

It is certified that error appears in the above-identified patent and that said Letters Patent are hereby corrected as shown below:

Column 1, lines 44-50, the formula II should appear as follows:

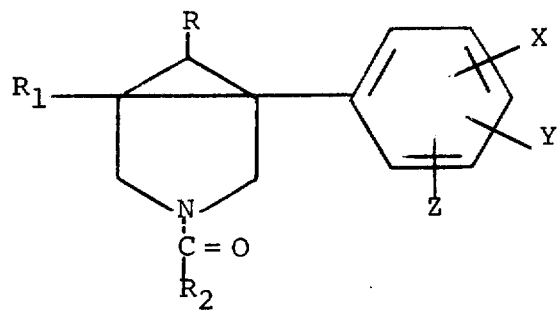

Column 1, lines 61-66, the formula I should appear as follows:

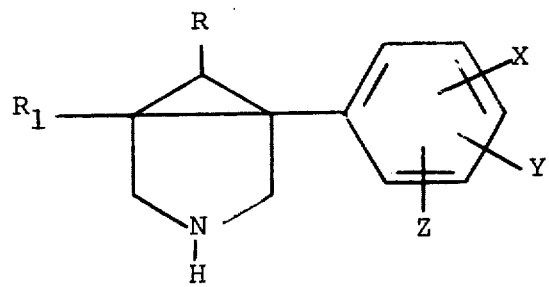

UNITED STATES PATENT OFFICE
CERTIFICATE OF CORRECTION

Patent No. 4,088,652　　　　　　　　Dated May 9, 1978

Inventor(s) William Joseph Fanshawe, et al.

It is certified that error appears in the above-identified patent and that said Letters Patent are hereby corrected as shown below:

Column 2, lines 9-15, the formula II should appear as follows:

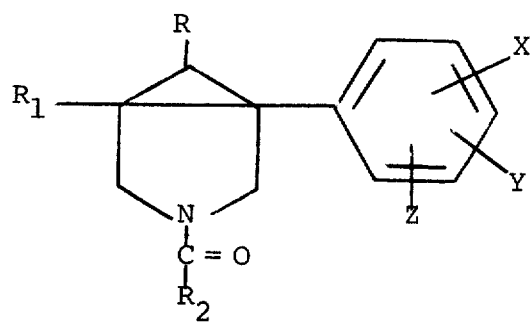

Claim 1, lines 25-31, the formula should appear as follows:

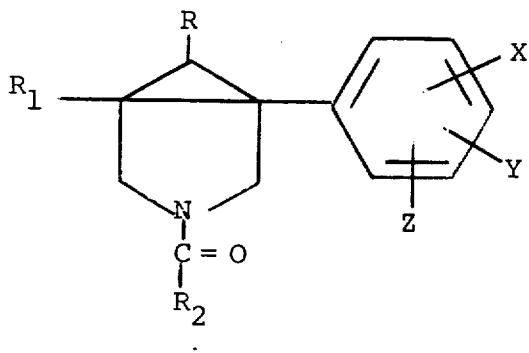

UNITED STATES PATENT OFFICE
CERTIFICATE OF CORRECTION

Patent No. 4,088,652    Dated May 9, 1978

Inventor(s) William Joseph Fanshawe, et al.

It is certified that error appears in the above-identified patent and that said Letters Patent are hereby corrected as shown below:

Claim 3, line 47, delete "yl--phenyl" and insert --yl-1-phenyl--.

Signed and Sealed this

Sixteenth Day of January 1979

[SEAL]

Attest:

RUTH C. MASON
*Attesting Officer*

DONALD W. BANNER
*Commissioner of Patents and Trademarks*